US009874512B2

(12) United States Patent
Delgado et al.

(10) Patent No.: US 9,874,512 B2
(45) Date of Patent: Jan. 23, 2018

(54) METHOD AND SYSTEM FOR GAS FLOW MITIGATION OF MOLECULAR CONTAMINATION OF OPTICS

(71) Applicant: KLA-Tencor Corporation, Milpitas, CA (US)

(72) Inventors: Gildardo Delgado, Livermore, CA (US); Terry Johnson, Livermore, CA (US); Marco Arienti, Livermore, CA (US); Salam Harb, Los Gatos, CA (US); Lennie Klebanoff, Dublin, CA (US); Rudy Garcia, Union City, CA (US); Mohammed Tahmassebpur, San Ramon, CA (US); Sarah Scott, Oakland, CA (US)

(73) Assignees: KLA-Tencor Corporation, Milpitas, CA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 686 days.

(21) Appl. No.: 14/466,516

(22) Filed: Aug. 22, 2014

(65) Prior Publication Data
US 2014/0362366 A1 Dec. 11, 2014

Related U.S. Application Data

(63) Continuation of application No. PCT/US2014/018344, filed on Feb. 25, 2014.
(Continued)

(51) Int. Cl.
| | | |
|---|---|---|
| G01N 21/15 | (2006.01) | |
| G01N 21/95 | (2006.01) | |
| G03F 7/20 | (2006.01) | |

(52) U.S. Cl.
CPC .......... *G01N 21/15* (2013.01); *G01N 21/9501* (2013.01); *G03F 7/70933* (2013.01); *G01N 2021/151* (2013.01)

(58) Field of Classification Search
CPC ............... G01N 21/15; G01N 21/9501; G01N 2021/151; G03F 7/70933
See application file for complete search history.

(56) References Cited

U.S. PATENT DOCUMENTS

| 6,714,624 B2 | 3/2004 | Fornaciari et al. |
| 6,747,729 B2 * | 6/2004 | Pril .......................... C01B 23/00 355/30 |

(Continued)

FOREIGN PATENT DOCUMENTS

| EP | 1398669 A1 | 3/2004 |
| EP | 1467602 A2 | 10/2004 |

(Continued)

*Primary Examiner* — Manuel L Barbee
(74) *Attorney, Agent, or Firm* — Simpson & Simpson, PLLC

(57) ABSTRACT

A computer-implemented method for determining an optimized purge gas flow in a semi-conductor inspection metrology or lithography apparatus, comprising receiving a permissible contaminant mole fraction, a contaminant outgassing flow rate associated with a contaminant, a contaminant mass diffusivity, an outgassing surface length, a pressure, a temperature, a channel height, and a molecular weight of a purge gas, calculating a flow factor based on the permissible contaminant mole fraction, the contaminant outgassing flow rate, the channel height, and the outgassing surface length, comparing the flow factor to a predefined maximum flow factor value, calculating a minimum purge gas velocity and a purge gas mass flow rate from the flow factor, the contaminant mass diffusivity, the pressure, the temperature, and the molecular weight of the purge gas, and introducing the purge gas into the semi-conductor inspection (Continued)

metrology or lithography apparatus with the minimum purge gas velocity and the purge gas flow rate.

16 Claims, 3 Drawing Sheets

Related U.S. Application Data

(60) Provisional application No. 61/768,898, filed on Feb. 25, 2013.

(56) References Cited

U.S. PATENT DOCUMENTS

| | | | |
|---|---|---|---|
| 7,334,602 B2 | 2/2008 | Ahn | |
| 7,511,287 B2 * | 3/2009 | Reece | H01J 37/3171 250/492.2 |
| 7,812,329 B2 | 10/2010 | Bykanov et al. | |
| 8,076,655 B2 | 12/2011 | Derra et al. | |
| 2002/0084425 A1 | 7/2002 | Klebanoff et al. | |
| 2004/0008328 A1 | 1/2004 | Akagawa et al. | |
| 2004/0062874 A1 | 4/2004 | Kim et al. | |
| 2005/0077474 A1 | 4/2005 | Finarov | |
| 2005/0098264 A1 | 5/2005 | Wolf et al. | |
| 2005/0122493 A1 * | 6/2005 | Tominaga | G03F 7/70933 355/30 |
| 2012/0025109 A1 | 2/2012 | Abhari et al. | |
| 2013/0004288 A1 | 1/2013 | Reed et al. | |

FOREIGN PATENT DOCUMENTS

| | | |
|---|---|---|
| JP | 2003163159 A | 6/2003 |
| KR | 20020060587 A | 7/2002 |
| WO | 2000049197 A1 | 8/2000 |
| WO | 2003/048000 A2 | 6/2003 |
| WO | 2006134512 A2 | 12/2006 |
| WO | 2008034582 A2 | 3/2008 |
| WO | 2009059614 A1 | 5/2009 |

* cited by examiner

METHOD AND SYSTEM FOR GAS FLOW MITIGATION OF MOLECULAR CONTAMINATION OF OPTICS

CROSS-REFERENCE TO RELATED APPLICATIONS

This application is a Continuation of International Patent Application Serial No. PCT/US2014/018344, filed on Feb. 25, 2014, which application claims priority of U.S. Provisional Patent Application No. 61/768,898, filed Feb. 25, 2013, which applications are incorporated herein by reference in their entirety.

STATEMENT REGARDING FEDERALLY SPONSORED RESEARCH OR DEVELOPMENT

This invention was developed with Government support under Contract No. DE-AC04-94AL85000 between Sandia Corporation and the U.S. Department of Energy. The U.S. Government has certain rights in this invention.

TECHNICAL FIELD

The present invention relates to a method and system for determining and creating an optimal gas flow in a semi-conductor inspection metrology or lithography apparatus to decrease the concentration of contaminants within the semi-conductor inspection metrology or lithography apparatus.

BACKGROUND

Extreme ultra-violet (EUV) light, which is defined as electromagnetic radiation with wavelengths between 124 nm and 10 nm, is used in next-generation photolithography systems to produce structures smaller than is possible with current ultra-violet light sources, such as excimer lasers. However, as EUV light is strongly attenuated by many substances, the path of EUV light from the light source to the location of its use is generally sealed and kept at a very low pressure to minimize attenuation of the EUV light.

The low-pressure environment within a semi-conductor inspection metrology or lithography apparatus using EUV light causes various contaminants to outgas from the walls and other surfaces which comprise the channel around the EUV light path. These contaminants, if not promptly removed, can foul the optics in the EUV light path or accumulate in the light path and result in the attenuation of the EUV light. Therefore, a purge gas is generally introduced into the EUV light path, causing the contaminants to either diffuse into the purge gas or be advected by the purge gas flow, after which, the purge gas and contaminants can be removed from the EUV light path by a vacuum pump.

For example, due to the low pressures found within apparatuses that use EUV light, such as semi-conductor inspection metrology or lithography apparatuses, desorption of contaminants, in the form of outgassing, occurs constantly. Metal surfaces near the optic elements can outgas significant amounts of water ($H_2O$), in the form of water vapor, at ambient temperature. Similarly, mirror adhesives, actuators, cables, and other mechanical elements can release hydrocarbon gases (HC) through gaps surrounding the mirrors. This desorption of contaminants causes various problems within these apparatuses, including degradation of optical performance in optic elements and attenuation of the EUV light via absorption by the contaminants. Optics requirements dictate very low partial pressures of these contaminant gases in the ducts, which may also be referred to as channels, through which the EUV light passes. These requirements can be achieved by using gas purging with the affected apparatus.

Typically, the purge gas is introduced into the EUV light path in a general flow and relies primarily on a high flow rate to remove the contaminants within the semi-conductor inspection metrology or lithography apparatus. However, this undirected, high flow rate approach has several drawbacks. First, extremely large and expensive pumps are needed to reduce the contaminants to acceptable levels, and frequently, these levels cannot even be achieved. Second, by introducing purge gas into the EUV light path in an undirected manner, there is no control over the flow of the purge gas within the semi-conductor inspection metrology or lithography apparatus. Certain regions, such as those that contain mirrors or other optics, require fastidious removal of contaminants so that the optics are not fouled. Finally, because undirected purge gas flow is relatively inefficient at removing contaminants, more purge gas must be introduced into the semi-conductor inspection metrology or lithography apparatus, which tends to attenuate the EUV light traveling through the same.

SUMMARY

According to aspects illustrated herein, there is provided a method for determining an optimized purge gas flow in a semi-conductor inspection metrology or lithography apparatus, comprising accepting, using a processor, a first input identifying a position of at least one input port for a semi-conductor inspection metrology or lithography apparatus, or identifying, using a processor, a position of at least one input port for a semi-conductor inspection metrology or lithography apparatus, accepting, using the processor, a second input identifying a position of at least one output port for the semi-conductor inspection metrology or lithography apparatus, or identifying, using the processor, a position of at least one output port for a semi-conductor inspection metrology or lithography apparatus, identifying, using the processor, at least one desorption surface in the semi-conductor inspection metrology or lithography apparatus, a desorption rate associated with the at least one desorption surface, and, a contaminant released from the at least one desorption surface, identifying, using the processor, at least one purge gas flow path, through the semi-conductor inspection metrology or lithography apparatus for a purge gas, calculating, using the processor and the respective identifications of the at least one desorption surface, the desorption rate, and the released contaminant, at least one minimum velocity and flow rate for a flow of purge gas, from the position of the at least one input port across the at least one desorption surface to the position of the at least one output port, sufficient to transport the released contaminant from a vicinity of the at least one desorption surface to the at least one output port, introducing the purge gas into the semi-conductor inspection metrology or lithography apparatus through the at least one input port with the at least one optimized gas velocity and gas flow rate, and transporting the released contaminant from the vicinity of the at least one desorption surface to the at least one output port.

According to aspects illustrated herein, there is provided a system for determining an optimized purge gas flow in a semi-conductor inspection metrology or lithography apparatus, comprising a processor arranged to accept a first input identifying a position of at least one input port for a semi-conductor inspection metrology or lithography apparatus, or identifying, using a processor, a position of at least one input port for a semi-conductor inspection metrology or lithography apparatus, accept a second input identifying a position of at least one output port for the semi-conductor inspection metrology or lithography apparatus, or identifying, using the processor, a position of at least one output port for a semi-conductor inspection metrology or lithography apparatus, identify at least one desorption surface in the semi-conductor inspection metrology or lithography apparatus, a desorption rate associated with the at least one desorption surface, and, a contaminant released from the at least one desorption surface, identify at least one purge gas flow path, through the semi-conductor inspection metrology or lithography apparatus for a purge gas, calculate using, the respective identifications of the at least one desorption surface, the desorption rate and the released contaminant, at least one minimum velocity and flow rate for a flow of purge gas, from the position of the at least one input port across the at least one desorption surface to the position of the at least one output port, sufficient to transport the released contaminant from a vicinity of the at least one desorption surface to the at least one output port, actuate the at least one input port to introduce the purge gas into the semi-conductor inspection metrology or lithography apparatus with the at least one optimized gas velocity and gas flow rate, and actuate the at least one output port to receive the purge gas flow and the released contaminant from the vicinity of the at least one desorption surface.

According to aspects illustrated herein, there is provided a method for determining an optimized purge gas flow in a semi-conductor inspection metrology or lithography apparatus, comprising receiving, using a processor, respective inputs in the nature of a permissible contaminant mole fraction, an expected contaminant outgassing flow rate associated with a contaminant, a mass diffusivity of the contaminant, an outgassing surface length, a permissible pressure, a permissible temperature, a channel height, and a molecular weight of a purge gas, calculating, using the processor, a flow factor based on the permissible contaminant mole fraction, the expected contaminant outgassing flow rate, the channel height, and the outgassing surface length, comparing, using the processor, the flow factor to a predefined maximum flow factor value, calculating, using the processor, a minimum required purge gas velocity and a purge gas mass flow rate from the flow factor, the mass diffusivity of the contaminant, the permissible pressure, the permissible temperature, and the molecular weight of the purge gas, and introducing the purge gas into the semi-conductor inspection metrology or lithography apparatus with the minimum required purge gas velocity and the purge gas flow rate.

According to aspects illustrated herein, there is provided a system for determining an optimized purge gas flow in a semi-conductor inspection metrology or lithography apparatus, comprising a processor arranged to receive input in the nature of a permissible contaminant mole fraction, an expected contaminant outgassing flow rate associated with a contaminant, a mass diffusivity of the contaminant, an outgassing surface length, a permissible pressure, a permissible temperature, a channel height, and a molecular weight of a purge gas, calculate a flow factor based on the permissible contaminant mole fraction, the expected contaminant outgassing flow rate, the channel height, and the outgassing surface length, compare the flow factor to a predefined maximum flow factor value, calculate a minimum required purge gas velocity and a purge gas mass flow rate from the flow factor, the mass diffusivity of the contaminant, the permissible pressure, the permissible temperature, and the molecular weight of the purge gas, and actuate at least one input port to introduce the purge gas into the semi-conductor inspection metrology or lithography apparatus with the minimum required purge gas velocity and the purge gas flow rate.

BRIEF DESCRIPTION OF THE DRAWINGS

Various embodiments are disclosed, by way of example only, with reference to the accompanying schematic drawing in which.

DETAILED DESCRIPTION

At the outset, it should be understood that the disclosure as claimed is not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the present disclosure.

Unless defined otherwise, all technical and scientific terms used herein have the same meaning as commonly understood to one of ordinary skill in the art to which this disclosure belongs. It should be understood that any methods, devices or materials similar or equivalent to those described herein can be used in the practice or testing of the disclosure. As used herein, by "computer" or "computing device" it is generally meant any analog or digital electronic device which includes a processor, memory, and/or a storage medium for operating or executing software or computer code.

Figure 1:
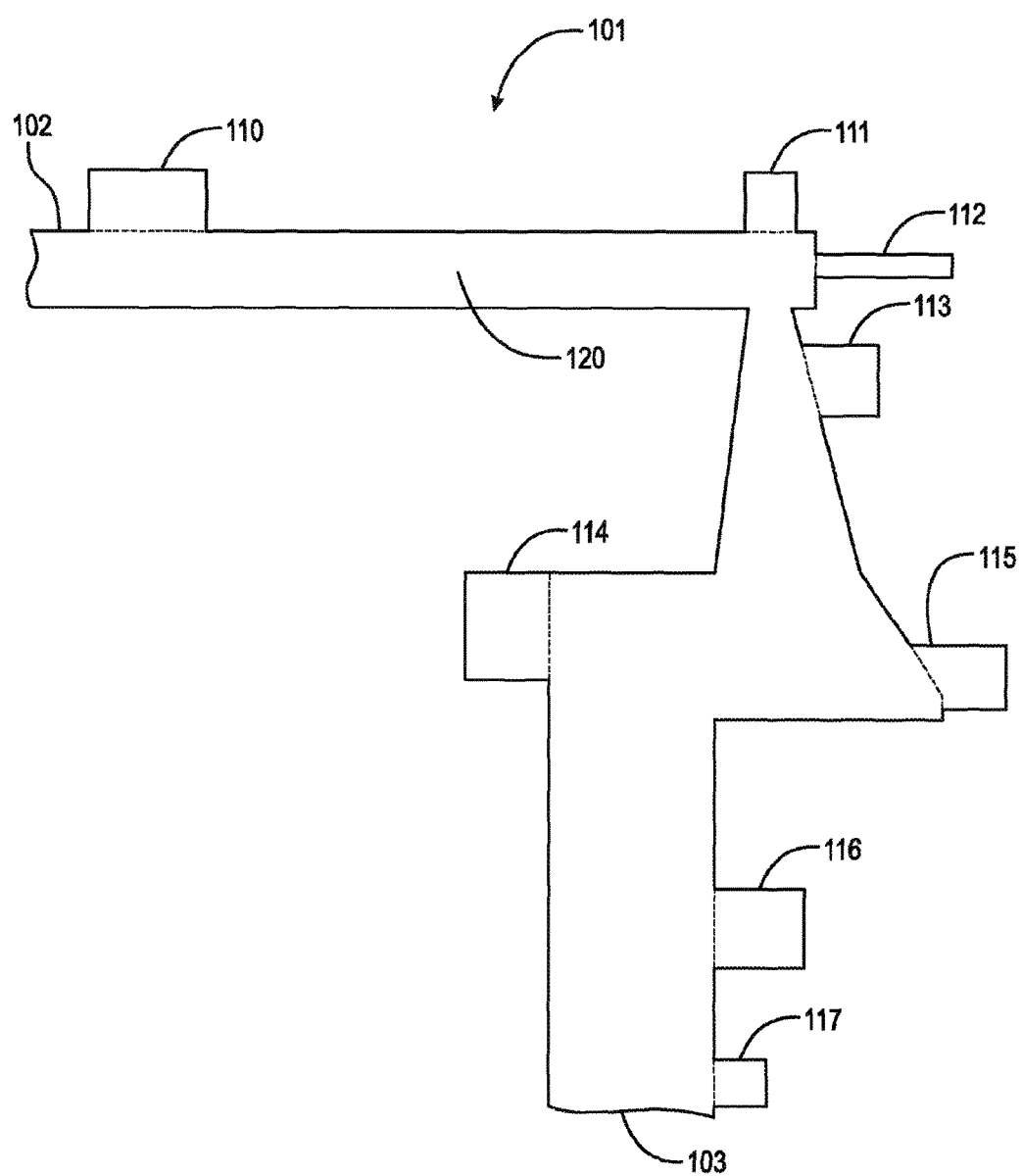
FIG. 1 is a schematic representation of a portion of a semi-conductor inspection metrology or lithography apparatus.

FIG. 1 depicts a schematic representation of a portion of typical semi-conductor inspection metrology or lithography apparatus 101. EUV light enters the portion of the semi-conductor inspection metrology or lithography apparatus 101 at entrance 102, travels through light path 120, and exits at exit 103. As described below, the entirety of light path 120 is maintained at a relatively low-pressure to reduce attenuation of the EUV light. To maintain the correct pressure, and to aid in the removal of contaminants, a plurality of gas ports 110-117 are arranged along light path 120 between entrance 102 and exit 103. Each of gas ports 110-117 may be an input port or an output port. Input ports are used to introduce a purge gas, such as hydrogen, into the portion of the semi-conductor inspection metrology or lithography apparatus 101. Output ports are used to remove the combination of purge gas and contaminants from the portion of the semi-conductor inspection metrology or lithography apparatus 101. By balancing the rate at which purge gas is introduced into the portion of the semi-conductor inspection metrology or lithography apparatus 101 and the rate at which the combination of purge gas and contaminants are removed from the same, it is possible to maintain a constant pressure within the portion of the semi-conductor inspection metrology or lithography apparatus 101.

Figure 2:
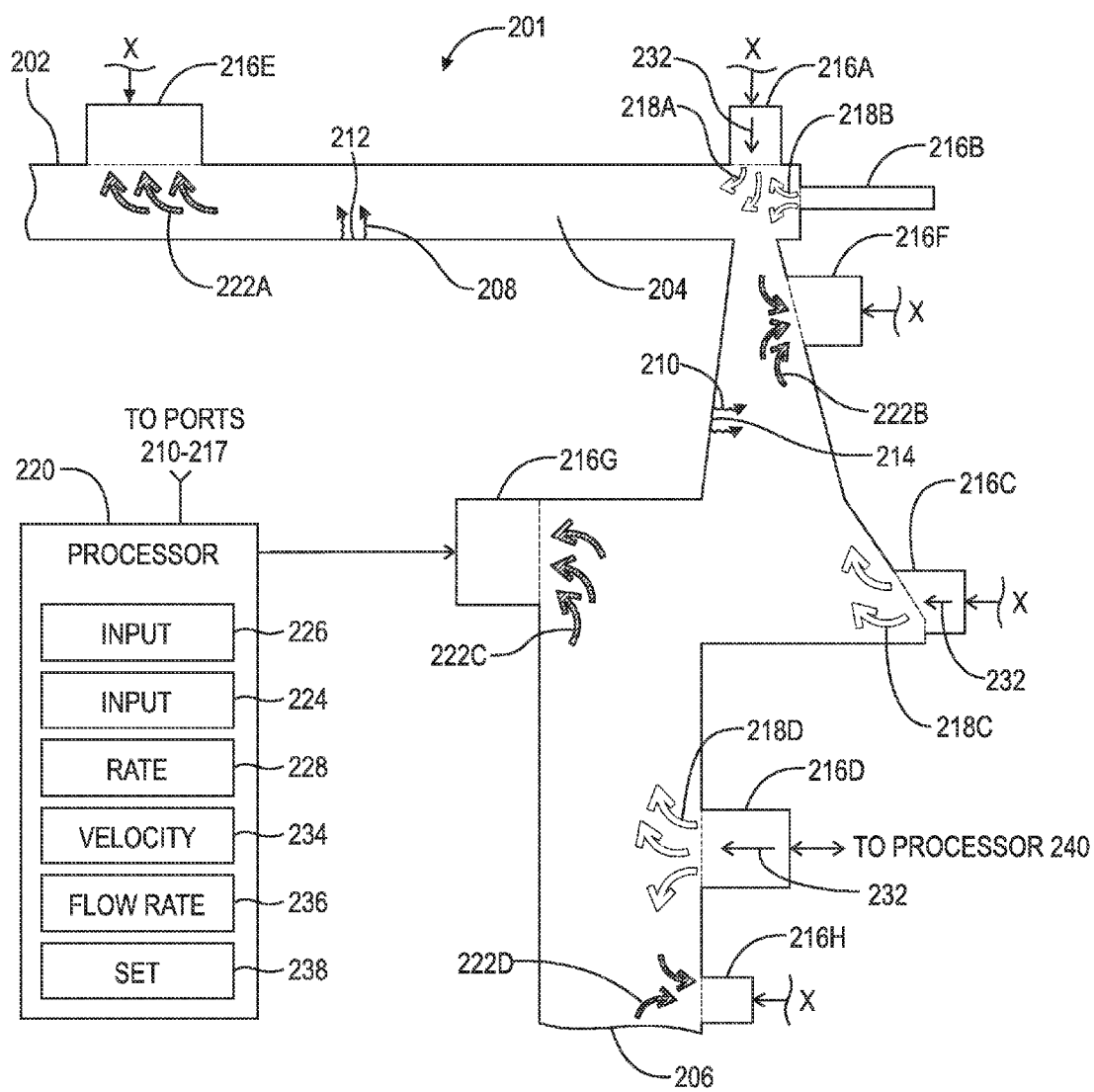
FIG. 2 is a schematic representation of a portion of a semi-conductor inspection metrology or lithography apparatus with an optimized purge gas flow; and, FIG. 3 is a graph containing representative data from a simulation, along with the curve fit derived from such data.

FIG. 2 depicts a schematic representation of a portion of a semi-conductor inspection metrology or lithography apparatus 201 in which a computer has calculated an optimized purge gas flow using the parameters specific to semi-conductor inspection metrology or lithography apparatus 201. EUV light enters the portion of the semi-conductor inspection metrology or lithography apparatus 201 at entrance 202, travels through light path 204, and exits at exit 206. Outgassing contaminants 208 and 210, are depicted generally by arrows with wavy lines and are being desorbed by surfaces included in semi-conductor inspection metrology or lithography apparatus 201. Contaminants 208 and 210 can be any contaminants known in the art, including, but not limited to, water, hydrocarbon gasses, acids, bases, inorganics, metal ions, metal hydrides, or silicon containing compounds including siloxanes. These surfaces are formed by metal components, mirror adhesives, actuators, cables, motors, stages, and other mechanical elements. Outgassing contaminants 208 and 210 are shown as emanating from specific surfaces 212 and 214, respectively, in semi-conductor inspection metrology or lithography apparatus 201 for purposes of illustration only. It should be understood that the number and location of contaminant outgassing surfaces are not limited to those shown in FIG. 2 and that other numbers and locations of contaminant outgassing surfaces are possible.

A plurality of gas ports 216 are arranged and actuated according to the optimized purge gas flow as calculated by the computer. In an example embodiment, gas ports 216A-216D are arranged as input ports and introduce purge gas flows 218A-218D, respectively, as depicted generally by arrows with no fill, into semi-conductor inspection metrology or lithography apparatus 201 at rates and velocities determined by the optimized purge gas flow as calculated by processor 220 as described below. Gas ports 216E-216H are arranged as output ports and remove combined purge gas/contaminant flows 222A-222D, as depicted generally by arrows with a hatched fill, from semi-conductor inspection metrology or lithography apparatus 201 at rates maintain a constant pressure within semi-conductor inspection metrology or lithography apparatus 201. It should be understood that the number and location of gas ports are limited to those shown in FIG. 2 and that other numbers and locations of gas ports are possible.

The following process is enabled in portion 201 using processor 220. Processor 220 is configured to accept input 224 identifying respective positions of input ports, for example ports 216A-216D, or processor 220 is configured to identify respective positions of input ports, for example ports 216E-216H. Processor 220 is configured to accept input 226 identifying respective positions of output ports, for example ports 216A-216D; or processor 220 is configured to identify respective positions of output ports, for example ports 216E-216H. Processor 220 is configured to identify: at least one desorption surface in portion 201 of a semiconductor inspection metrology or lithography apparatus (for example, surfaces 212 and 214); desorption rate 228 associated with, for example, surfaces 212 and 214; and for example, contaminants 208 and 210 released from surfaces 212 and 214.

Processor 220 is configured to identify at least one purge gas flow path 218, for example, including purge gas flows 218A-218D and combined purge gas/contaminant flows 222A-222D, through portion 201 for purge gas 232. Purge gas 232 can be any purge gas known in the art, including but not limited to hydrogen and helium. Processor 220 is configured to calculate using identifications of desorption surfaces, desorption rate 228, and contaminants, at least one minimum velocity 234 and flow rate 236 for a flow of purge gas 232. Velocity 234 and rate 236 are from positions of one of more input ports across the at least one desorption surface to the positions of one or more output ports. Velocity 234 and rate 236 are sufficient to transport released contaminants from a vicinity of the at least one desorption surface to the at least one output port. Processor 220 is configured to actuate the at least one input port, for example, ports 216A-216D, to introduce the purge gas 232, for example, purge gas flows 218A-218D into portion 210 with velocity 234 and flow rate 236 and actuate the at least one output port, for example, ports 216A-216D, to receive the purge gas flow and the released contaminant, for example, combined purge gas/contaminant flows 222A-222D, from the vicinity of the at least one desorption surface.

In an example embodiment, processor 220 is configured to identify set 238 of channel dimensions within portion 201. In an example embodiment, processor 220 is configured to calculate velocity 234 and flow rate 236 using set 238 of channel dimensions.

In an example embodiment, processor 220 is configured to determine, using identifications of desorption surfaces, desorption rate 228, and contaminants, at least one optimal input port position, for example respective positions of ports 216A-216D and introduce purge gas 232 at the optimal input port locations. In an example embodiment, processor 220 is configured to determine, using identifications of desorption surfaces, desorption rate 228, and contaminants, at least one optimal output port position, for example respective positions of ports 216E-216G and remove combined purge gas/contaminant flows, for example flows 222A-222D, from portion 201.

In an embodiment, such desorption is addressed by creating a flow of purge gas within the apparatus, which flow carries away the contaminants through a combination of advection and diffusion and is eventually extracted by a vacuum pump. In such an embodiment, a flow of a purge gas, such as hydrogen ($H_2$), helium (He), or other gasses, is directed across the face or perpendicular to the face of an optic element to prevent molecular contamination of the optic element while, at the same time, minimizing the attenuation of the EUV light as it passes through the gas. Channels are used to direct bulk $H_2$ flow across or at optics, or alternately, one or more gas nozzles are aimed at individual optics and the $H_2$ flow is tailored specifically for the geometry of the optic. The flow of hydrogen gas can be designed reduce the partial pressure of $H_2O$ and other contaminants and to remove any hydrocarbon or water contamination that may exist in the residual gas above the optic element. Using ultrapure purge gas ensures that no additional contaminants are introduced into the apparatus. Although many different gasses are acceptable to use as purge gas, due to hydrogen's low rate of light absorption in the EUV range, when it is used as a purge gas, the performance of the optic element or mask within the apparatus is essentially unaffected. Modeling studies have indicated that this approach is capable of reducing the partial pressure of contaminants above an optic element by a factor of 20 or more.

The exact amount of purge gas flow depends on the geometry of the interior of the apparatus and on the absorption and desorption properties of all internal surfaces. Three-dimensional flow dynamics calculations and accurate models for surface behavior are therefore necessary. Molecular kinetics effects become relevant when the Knudsen number approaches the order of 0.1. For very large Knudsen numbers, e.g., greater than 10, the rate of intermolecular collisions is very small compared to the rate of molecule-wall collisions and transport becomes ballistic. The regime existing when the Knudsen number is between 0.1 and 10 is known as the transition regime, and it is typically the most challenging to model. In this regime, nonlocal transport is important while collisions between molecules are nontrivial. The embodiment reflects a model for wall slip conditions that is suited to moderate Knudsen numbers, in which slip conditions are taken to exist across the Knudsen layer, which is of the order of one mean free path in thickness.

From the closed-form solutions of the mass, momentum, and energy flux equations, the velocity slip conditions for a single species gas are:

$$u_s = \frac{2-\sigma}{2} \frac{5\pi}{16} \lambda \left( \frac{\partial u}{\partial y} + \frac{\partial v}{\partial x} \right) + \frac{15}{32} \sqrt{\frac{\pi}{2} RT} \frac{\lambda_s}{T} \frac{\partial T}{\partial x}$$

and $$v_s = \frac{2-\sigma}{2} \frac{5\pi}{16} \lambda \left( \frac{\partial w}{\partial y} + \frac{\partial v}{\partial z} \right) + \frac{15}{32} \sqrt{\frac{\pi}{2} RT} \frac{\lambda_s}{T} \frac{\partial T}{\partial z}$$

where u, v, w, are the three component of velocity in the x, y, z directions, in which y is the normal of the surface and x and z are parallel to the surface, T is the temperature and R is the gas constant. The constant $\sigma$ is the accommodation coefficient, which denotes the fraction of diffusely reflected molecules. In most surfaces of practical interest, the fully accommodating value $\sigma=1$ is chosen. The parameter $\lambda$ is expressed as the viscosity-based mean free path $$\lambda = \frac{\mu}{P} \sqrt{\frac{\pi RT}{2}}$$

where P is the absolute pressure and $\mu$ the dynamic viscosity.

The magnitude of the slip velocity, when ignoring temperature variations along the surface, therefore takes the simplified finite-difference form $$V_{slip} \cong A_{slip} \frac{V_t^{cell} - V_{slip}}{\delta}.$$

The parameter $\delta$ is chosen as the distance of the cell centroid to the nearest surface for the boundary cells, $$A_{slip} \equiv \lambda \frac{2-\sigma}{2}.$$

In vector form, the slip velocity can be expressed by using the cell-based surface normal n in the form:

$$V_{slip} = \frac{A_{slip}}{1+A_{slip}} (V^{cell} - (V^{cell} \cdot n) \cdot n)$$

In order to accurately model the conditions within the apparatus, the amount of partial pressure from water and other contaminants that accumulate at an optical surface in steady-state conditions must be estimated. Optics duration requirements dictate very low partial pressures of contaminants. Such pressures can be achieved by introducing a regulated amount of hydrogen, or other purge gases, into the apparatus for purging. The optimal amount of purge gas flow depends on the geometry of the EUV apparatus and the absorption and desorption properties of all internal surfaces.

Using computational fluid dynamic software tools running on a computing device, it is possible to simulate the effects of different duct geometry factors and surface emission properties in a series of increasingly more realistic simulations for water and hydrocarbon gasses in a flow of hydrogen purge gas. The objective of these simulations is to develop a characteristic curve of contaminant partial pressure versus hydrogen flow as a way to assist the design of the EUV apparatus by collapsing geometrical factors and physical properties of desorption in non-dimensional parameters linked by a correlation.

In setting up the simulation, certain assumptions about the behaviors and conditions within the EUV apparatus are made. For example, it is assumed that the gas within the EUV apparatus is represented as a mixture of hydrogen and water vapor and described by the perfect gas equation of state. It is also assumed that desorption is modeled by a fixed wall flux of water vapor, independent from the gas state. These assumptions simplify the simulation and provide substantially accurate results. However, more physically complete mechanisms, including calculating the dependence of absorption on the monolayer status and the effect of local pressure can also be implemented using computational fluid dynamic software tools.

The diffusion coefficient for a binary gas mixture at low to moderate pressures can be estimated using kinetic theory, and results in the following relation:

$$D_{1,2} = 1.883 \cdot 10^{-22} \frac{T^{3/2}}{P l_{1,2}^2 \Omega_D} \sqrt{\frac{MW_1 + MW_2}{MW_1 MW_2}}$$

where $D_{1,2}$ is the binary diffusion coefficient (m²/s), T is the absolute temperature in Kelvin, $MW_1$ and $MW_2$ are the molar masses of species 1 and 2, P is the absolute pressure in Pascals, $l_{1,2}$ is a characteristic length of the mixture in meters, and $\Omega_D$ is the dimensionless collision integral for diffusion. The characteristic length $l_{1,2}$ is estimated according to the average of the Lennard-Jones potential characteristic lengths for species 1 and 2:

$$l_{1,2} = \frac{l_1 + l_2}{2}$$

The collision integral for diffusion $\Omega_D$ is a function of the dimensionless temperature:

$$\tilde{T} = \frac{k_B T}{\varepsilon_{1,2}}$$

where $k_B$ is the Boltzmann's constant $1.381 \times 10^{-23}$ J/K and $\varepsilon_{1,2}$ is a characteristic mixture energy parameter. The mixture energy parameter $\varepsilon_{1,2}$ can be estimated in terms of the Lennard-Jones potential characteristic energies for species 1 and 2 ($\varepsilon_1$ and $\varepsilon_2$) according to $\varepsilon_{1,2} = \sqrt{\varepsilon_1 \varepsilon_2}$.

Thus, for a given mixture at isothermal conditions, the mass diffusion coefficient inversely depends on the absolute pressure, $D_{1,2} \cdot P \sim \text{const}$. Furthermore, $D_{1,2}$ decreases with the square of the characteristic length of one or both species. An increase of the Lennard-Jones energy parameter corresponds non-linearly to an increase of the collision integral, and this increase in turn reduces $D_{1,2}$. Because of the harmonic mean between molar masses, if one of the species is much lighter than the other, then the diffusion coefficient does not change appreciably with the molar mass of the heavier gas, $MW_2$. The molecular diffusivity $D_m$ of component m is calculated as:

$$D_m = \frac{\sum_{i=1,N, i \neq m} X_i M_{W_i}}{M_W \sum_{i=1,N, i \neq m} \frac{X_i}{D_{i,m}}}$$

where $M_W$ is the local molecular weight of the mixture and $M_{Wi}$ is the molecular weight of component i.

Given these conditions at the boundary, it is important to determine whether the estimation correctly integrates the flux wall source term and correctly propagates water vapor, or other contaminants, inside the domain in question. Two cases are considered: one in the diffusion-dominated regime and the second in the advection-dominated regimes. In both cases, $H=0.075$ m and $Q_v=4.394$ m$^3$/s. The width of the channel is established as 2H. In the case of water contaminant and hydrogen purge gas, the binary diffusion coefficient of water in hydrogen is $D=0.4$ m$^2$/s in the first case and $D=0.004$ m$^2$/s in the second. The respective Peclet numbers are Pe=73 and Pe=7300. Also, $\lambda=1$ m$^{-1}$ and N=1e-7 kmol/m$^3$. The molar concentration of water for Pe=73 is shown in FIG. 5. In the diffusion-dominated regime, the simulation shows that the water vapor boundary layer completely reaches the centerline of the duct and that its distribution describes a full arc of parabola.

In the advection-dominated regime, water vapor is swept away by hydrogen as soon as it is formed at the surface. The boundary layer of the vapor is very thin and near zero concentration is reached in a band centered along the centerline of the duct. This simulation is consisten with the Navier-Stokes equations for mulitspecies flow, and therefore, is a suitable model to study advection/diffusion problems with added source terms.

Building on this simulation, a model that distinguishes between a non-emitting surface, such as a mirror, and contaminant-emitting surfaces, such as the metal walls of the EUV apparatus, while keeping the two-dimensional duct model can be created. The two-dimensional geometry is simple enough that a direct comparison with the direct simulation Monte Carlo method can be carried out. Simplifying the geometry also allows a fast simulation turnover time, making it possible to conduct a parametric study on the effect of non-outgassing/outgassing area ratio and duct height. Given the prevalence of water as a contaminant in EUV apparatuses, the metric used in these simulations is the average partial pressure of $H_2O$ on an optic element, such as a mirror. The metal walls of the EUV apparatus are assumed to be outgassing at a given rate per surface area.

The simulations with varying EUV apparatus geometry show the contaminant species distribution within the EUV apparatus typically takes longer to reach a steady state, well after the residuals of the simulation have stabilized to a prescribed small number. When the simulation is run with 1 mTorr mean pressure and 24.6 mbar/lit-s of hydrogen flow, the inlet boundary condition is a parabolic velocity prescription, and the outlet is set as a constant pressure boundary condition, the simulation shows that the flow at the exit is mostly axial. Therefore a straight channel geometry for the EUV apparatus was sufficient in the majority of cases. At very high velocity, however, a diverging grid can be added at the downstream end of the domain to maintain a sufficiently uniform pressure profile at the exit.

A broader set of conditions is considered. In these cases, the duct average pressure is 1 mTorr, 10 mTorr, or 45 mTorr, and the outgassing flux takes one of two values: $4.071 \times 10^{-11}$ kg/s-m$^2$ or $4.071 \times 10^{-10}$ kg/s-m$^2$. The simulation varies the rate of the inflow of hydrogen purge gas from between 0.002 mbar-lit/s to 100 mbar-lit/s, which range covers the diffusion-dominated regime and the advection-dominated regime. The hydrogen inflow is calculated from the parabolic velocity profile by assuming a square duct section. For all the conditions used in the simulation, the partial pressure of water is always established as less than $3 \times 10^{-7}$ Torr. The simulation may also be run with variations in other parameters, such as non-outgassing surface length (e.g., surface consisting of mirrors) or duct height.

The simulation indicates that the concentration of water vapor decreases as the purge gas flow rate increases. However, at sufficiently low purging rates, small increases of hydrogen purge gas flow do little to decrease the $H_2O$ content. A transition to linear behavior is observed for larger purging rates, but the value of this transition point depends on the average pressure of the duct. Decreasing the duct pressure delays the appearance of the linear regime. The results of the simulation also indicate that, as the velocity with which the hydrogen purge gas is introduced into the EUV apparatus increases, eventually this linear regime ends and the contaminant concentration becomes constant. At that point, an increase in purging flow rate does not substantially affect the vapor concentration.

When the wall flux of water vapor is increased tenfold, the $H_2O$ partial pressure increases by approximately the same factor. Similarly, the addition of more emitting surface metal area proportionally increases the $H_2O$ concentration. These results suggest how to collapse the data so that a flow rate/partial pressure relation can be also used for different flow conditions or duct geometries. These variables X and Y can be defined as:

$$X = \frac{V_{inlet}}{D} = \frac{\dot{m}_{H_2}/HW}{\rho_{inlet} D}$$

and $$Y = \frac{X_{H_2O}}{h_w W L_{emitting}} = \frac{P_{H_2O}}{P_{mean} h_w W L_{emitting}}$$

where W is the spanwise width of the duct, so that W*H is the cross-sectional area of the duct. It is possible, for the most part, to successfully collapse the data points produced by running the simulation with different parameters onto a single curve. One notable exception to this general trend appears to be the set of data corresponding to 1 mTorr for the configuration with added outgassing metal surfaces. The parameters X and Y are dimensional: X has units of inverse length; Y has units of inverse of mass flux. This indicates that additional variables need to be included to obtain the most general formulation.

Based on the data produced by running the simulation, an empirical correlation between X and Y is found in the form $Y=19{,}000e^{-0.21X}$, where the two coefficients are also dimensional. This correlation incorporates the effects of channel pressure, outgassing rate, and the amount of emitting surface in the channel. The exponential term reflects the vanishing efficacy of purging below a certain flow rate for an assigned duct pressure. Equivalently, the correlation emphasizes the increasing purging efficacy when duct pressure is increased, which is due to the corresponding decrease in effective diffusion. The validity of this correlation can only be confirmed for X values of less than 100 m$^{-1}$, as results at higher inlet velocities indicate that larger purging flows become increasingly less effective in removing contaminants.

With the curve resulting from the data generated by the simulation, it is possible to calculate an optimized purge gas velocity and purge gas flow rate, by providing values for the channel height, the length of the outgassing surfaces, the desired mole fraction of the contaminants (e.g., the desired partial pressure of H$_2$O divided by total pressure), and the outgassing rate of the contaminants from the surrounding metal (i.e., h$_w$).

Figure 3:
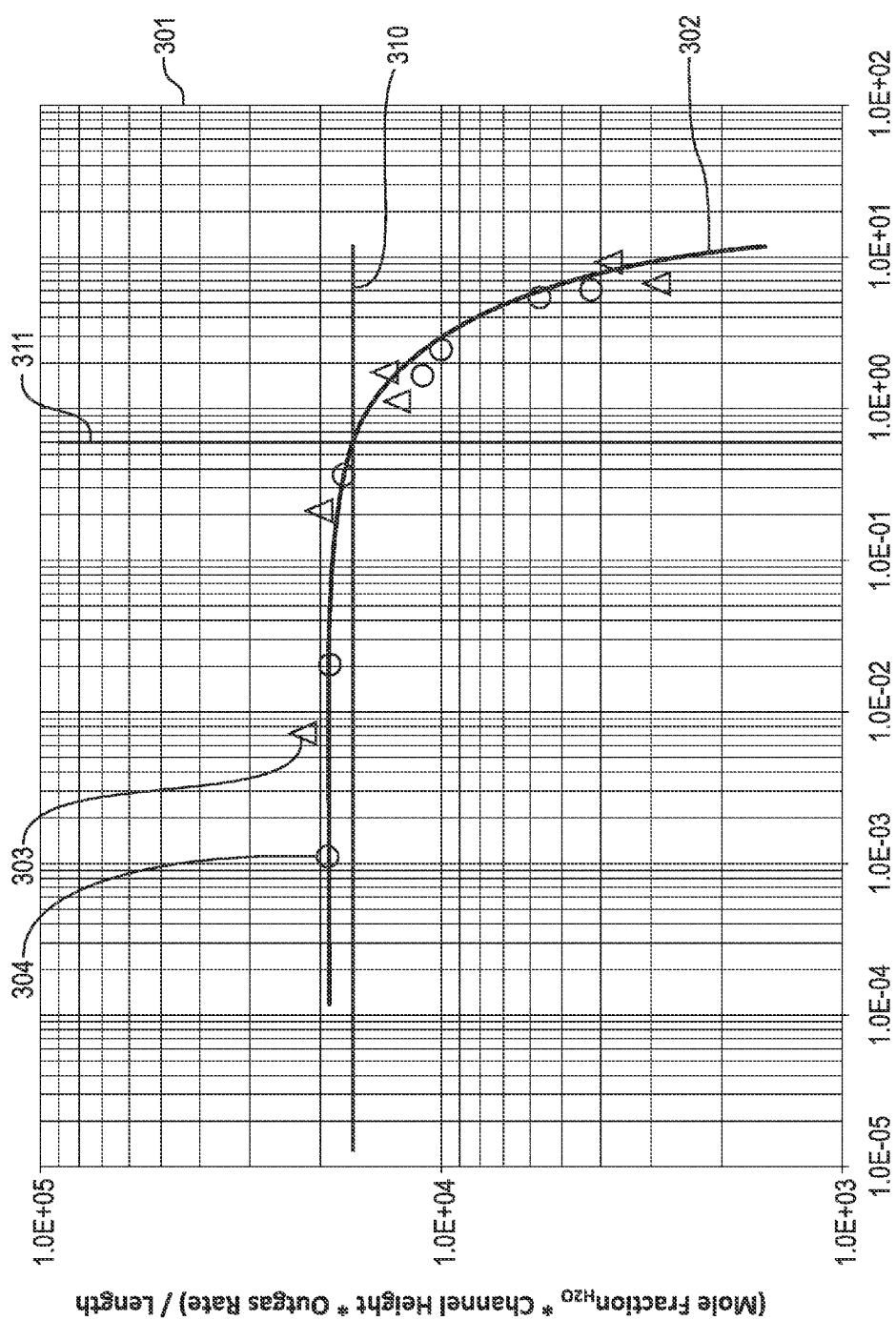

FIG. 3 shows representative data from the simulation, along with the curve fit derived from such data. Graph 301 has both the scatterplot data produced by the simulation and curve fit 302 derived from such data, wherein triangle points 303 represent the data produced by the simulation when run with a moderate duct average pressure and high contaminant outgassing rate and circle points 304 represent data produced by the simulation when run with low duct average pressure and low contaminant outgassing rate. The parameter sets resulting in triangle points 303 and circle points 304 have been chosen only as representative for purposes of illustration in FIG. 3, and varying the input parameters sets for the simulation will result in data that also supports curve fit 302. As used with the curve fit, we can define the following values:

$$Y = \frac{\text{Mole Fraction} * \text{Channel Height} * \text{Outgas Rate}}{\text{Length}}$$

$$X = \frac{\text{Mean Velocity over the Mirror}}{\text{Effective Mass Diffusivity}}$$

Thus, in order to determine if a purge flow is needed, the value Y is calculated from the values for the channel height, the length of the outgassing surfaces, the desired mole fraction of the contaminants, and the outgassing rate of the contaminants from the surrounding metal and compared to the maximum value of the curve fit, which is defined as $Y_{MAX}=19{,}000$. If Y is greater than $Y_{MAX}$, then no flow is needed, though in reality, a nominal flow value will be required to maintain the total pressure level in the channel. If Y is less than $Y_{MAX}$, then the following calculation is performed:

$$X = -\frac{1}{0.21} \ln\left(\frac{Y}{19{,}000}\right)$$

From X, the required purge gas velocity can be found by converting the mean velocity to flow rate per channel cross-section using the following equation:

$$\dot{m}_{H2} = \rho A X D$$

where A is the channel cross-sectional area. The gas density is determined from the ideal gas law (with universal gas constant R$_U$)

$$\rho = \frac{PM_W}{R_U T}$$

Referring again to FIG. 3, this process is illustrated by Y-value line 310, in which value for Y is determined based on the input of the values discussed above. If the calculated Y value is greater than $Y_{MAX}$, then Y-value line 310 will not intersect with curve fit 302. However, if the calculated Y value is less than $Y_{MAX}$, then the X-value of the point of intersection with curve fit 302 provides the value for X, as indicated by X-value line 311. Accordingly, by simulating the advection and diffusion of purge gas and contaminants in the presence of a boundary source using a comparatively simple two-dimensional duct model, it is possible to optimizing the flow of purge gas within an EUV apparatus without the need for a more computationally expensive three-dimensional computational fluid dynamics simulation. This type of analysis can be used to determine the optimal purge gas flow parameters, including physical positions for input and output ports. Therefore, if the above-discussed simulation is run on an EUV apparatus prior to the finalization of its design, the physical positions of the input and output ports may be optimized using the data returned by the simulation. As part of this calculation, the pressure at each open port is specified as boundary condition while the corresponding flow rate is not known in advance. The steady-state solution is reached when the net inlet and outlet calculated from all the ports are equal.

Additionally, as a result of knowing the density field within the EUV apparatus, the EUV transmission can be calculated directly. The transmission coefficient is evaluated by integrating the number density n along the beam:

$$\omega = \exp\left(-\sigma \int n(s)ds\right) = \exp\left(-\frac{\sigma N_A}{M_{H2}} \int \rho(s)ds\right)$$

where the cross-section for typical purge gas hydrogen is $\sigma=4.927\times10^{-24}$ m$^2$ and the molecular mass of hydrogen is $M_{H2}=2.0159$ g/mole. $N_a$ is the Avogadro number. The density $\rho(s)$ is calculated as part of the simulation and integrated numerically along a segment forming a part of the EUV light beam's path. The total transmission is calculated as the product of the transmissions on individual line probes within the EUV apparatus.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for determining an optimized purge gas flow in a semi-conductor inspection metrology or lithography apparatus, comprising:

accepting, using a processor, a first input identifying a position of at least one input port for a semi-conductor inspection metrology or lithography apparatus; or identifying, using a processor, a position of at least one input port for a semi-conductor inspection metrology or lithography apparatus;

accepting, using the processor, a second input identifying a position of at least one output port for the semiconductor inspection metrology or lithography apparatus; or identifying, using the processor, a position of at least one output port for a semi-conductor inspection metrology or lithography apparatus;

identifying, using the processor:
   at least one desorption surface in the semi-conductor inspection metrology or lithography apparatus;
   a desorption rate associated with the at least one desorption surface; and,
   a contaminant released from the at least one desorption surface;

identifying, using the processor, at least one purge gas flow path, through the semi-conductor inspection metrology or lithography apparatus for a purge gas;

calculating, using the processor and the respective identifications of the at least one desorption surface, the desorption rate, and the released contaminant, at least one minimum velocity and flow rate for a flow of purge gas, from the position of the at least one input port across the at least one desorption surface to the position of the at least one output port, sufficient to transport the released contaminant from a vicinity of the at least one desorption surface to the at least one output port;

introducing the purge gas into the semi-conductor inspection metrology or lithography apparatus through the at least one input port with the at least one minimum velocity and gas flow rate; and, transporting the released contaminant from the vicinity of the at least one desorption surface to the at least one output port.

2. The method recited in claim 1, further comprising:
identifying, using the processor, a set of channel dimensions within the semi-conductor inspection metrology or lithography apparatus.

3. The method recited in claim 2, further comprising:
calculating, using the processor and the set of channel dimensions, the at least one minimum velocity and flow rate.

4. The method recited in claim 1, further comprising:
determining, using the processor and the respective identifications of the at least one desorption surface, the desorption rate, and the released contaminant, at least one optimal input port position; and,
introducing the purge gas at the at least one optimal input port.

5. The method recited in claim 1, further comprising:
determining, using the processor and the respective identifications of the at least one desorption surface, the desorption rate, and the released contaminant, at least one optimal output port position; and,
transporting the released contaminant from the vicinity of the at least one desorption surface to the at least one optimal output port.

6. The method of claim 1, wherein the purge gas is selected from the group consisting of hydrogen and helium.

7. The method of claim 1, wherein the contaminant is selected from the group consisting of water and hydrocarbon gasses.

8. A system for determining an optimized purge gas flow in a semi-conductor inspection metrology or lithography apparatus, comprising:
a processor arranged to:
   accept a first input identifying a position of at least one input port for a semi-conductor inspection metrology or lithography apparatus; or identifying, using a processor, a position of at least one input port for a semi-conductor inspection metrology or lithography apparatus;
   accept a second input identifying a position of at least one output port for the semi-conductor inspection metrology or lithography apparatus; or identifying, using the processor, a position of at least one output port for a semi-conductor inspection metrology or lithography apparatus;
   identify:
      at least one desorption surface in the semi-conductor inspection metrology or lithography apparatus;
      a desorption rate associated with the at least one desorption surface; and,
      a contaminant released from the at least one desorption surface;
   identify at least one purge gas flow path, through the semi-conductor inspection metrology or lithography apparatus for a purge gas;
   calculate using, the respective identifications of the at least one desorption surface, the desorption rate and the released contaminant, at least one minimum velocity and flow rate for a flow of purge gas, from the position of the at least one input port across the at least one desorption surface to the position of the at least one output port, sufficient to transport the released contaminant from a vicinity of the at least one desorption surface to the at least one output port;
   actuate the at least one input port to introduce the purge gas into the semi-conductor inspection metrology or lithography apparatus with the at least one minimum velocity and gas flow rate; and,
   actuate the at least one output port to receive the purge gas flow and the released contaminant from the vicinity of the at least one desorption surface.

9. The system recited in claim 8, wherein the processor is arranged to identify a set of channel dimensions within the semi-conductor inspection metrology or lithography apparatus.

10. The system recited in claim 9, wherein the processor is arranged to calculate the at least one minimum velocity and flow rate using the set of channel dimension.

11. The system recited in claim 8, wherein the processor is arrange to:
   determine at least one optimal input port position using the respective identifications of the at least one desorption surface, the desorption rate, and the released contaminant; and,
   actuate the at least one input port to introduce the purge gas.

12. The system recited in claim 8, wherein the processor is arrange to:
   determine, using the respective identifications of the at least one desorption surface, the desorption rate, and the released contaminant, at least one optimal output port position; and,
   actuate the at least one optimal output port to remove the purge gas and the released contaminant from the semi-conductor inspection metrology or lithography apparatus.

13. The system of claim 8, wherein the purge gas is selected from the group consisting of hydrogen, helium, and mixed gas containing hydrogen and helium.

14. The system of claim 8, wherein the contaminant is selected from the group consisting of water, hydrocarbon gasses, acids, bases, inorganics, metal ions, metal hydrides, and silicon containing compounds including siloxanes.

15. A method for determining an optimized purge gas flow in a semi-conductor inspection metrology or lithography apparatus, comprising:
- receiving, using a processor, respective inputs in the nature of a permissible contaminant mole fraction, an expected contaminant outgassing flow rate associated with a contaminant, a mass diffusivity of the contaminant, an outgassing surface length, a permissible pressure, a permissible temperature, a channel height, and a molecular weight of a purge gas;
- calculating, using the processor, a flow factor based on the permissible contaminant mole fraction, the expected contaminant outgassing flow rate, the channel height, and the outgassing surface length;
- comparing, using the processor, the flow factor to a predefined maximum flow factor value;
- calculating, using the processor, a minimum required purge gas velocity and a purge gas mass flow rate from the flow factor, the mass diffusivity of the contaminant, the permissible pressure, the permissible temperature, and the molecular weight of the purge gas; and,
- introducing the purge gas into the semi-conductor inspection metrology or lithography apparatus with the minimum required purge gas velocity and the purge gas flow rate.

16. A system for determining an optimized purge gas flow in a semi-conductor inspection metrology or lithography apparatus, comprising:
- a processor arranged to:
  - receive input in the nature of a permissible contaminant mole fraction, an expected contaminant outgassing flow rate associated with a contaminant, a mass diffusivity of the contaminant, an outgassing surface length, a permissible pressure, a permissible temperature, a channel height, and a molecular weight of a purge gas;
  - calculate a flow factor based on the permissible contaminant mole fraction, the expected contaminant outgassing flow rate, the channel height, and the outgassing surface length;
  - compare the flow factor to a predefined maximum flow factor value;
  - calculate a minimum required purge gas velocity and a purge gas mass flow rate from the flow factor, the mass diffusivity of the contaminant, the permissible pressure, the permissible temperature, and the molecular weight of the purge gas; and,
  - actuate at least one input port to introduce the purge gas into the semi-conductor inspection metrology or lithography apparatus with the minimum required purge gas velocity and the purge gas flow rate.

* * * * *